US006587798B2

(12) United States Patent
Kersey et al.

(10) Patent No.: US 6,587,798 B2
(45) Date of Patent: Jul. 1, 2003

(54) METHOD AND SYSTEM FOR DETERMINING THE SPEED OF SOUND IN A FLUID WITHIN A CONDUIT

(75) Inventors: Alan D. Kersey, S. Glastonbury, CT (US); Daniel L. Gysling, Glastonbury, CT (US); James D. Paduano, Arlington, MA (US)

(73) Assignee: Weatherford/Lamb, Inc., Houston, TX (US)

( * ) Notice: Subject to any disclaimer, the term of this patent is extended or adjusted under 35 U.S.C. 154(b) by 0 days.

(21) Appl. No.: 09/997,221

(22) Filed: Nov. 28, 2001

(65) Prior Publication Data

US 2002/0100327 A1 Aug. 1, 2002

Related U.S. Application Data

(60) Provisional application No. 60/250,997, filed on Dec. 4, 2000.

(51) Int. Cl.$^7$ .............................................. G06F 19/00
(52) U.S. Cl. ........................................ 702/50; 73/61.79
(58) Field of Search .......................... 702/68.5, 54–56, 702/66, 75–79, 124, 126, 110–112, 142–143, 183, 184; 73/861.17, 861.18, 861.23, 861.28, 152.32, 152.46, 61.79, 54.41, 861.29; 181/105, 143

(56) References Cited

U.S. PATENT DOCUMENTS

| | | | |
|---|---|---|---|
| 3,952,578 A | | 4/1976 | Jacobs ........................ 73/64.1 |
| 4,320,659 A | | 3/1982 | Lynnworth et al. ........... 73/589 |
| 5,770,806 A | * | 6/1998 | Hiismaki .................. 73/861.29 |
| 5,948,959 A | | 9/1999 | Peloquin |
| 6,354,147 B1 | * | 3/2002 | Gysling et al. ............. 73/61.79 |
| 6,378,357 B1 | * | 4/2002 | Han et al. ................... 73/54.41 |

FOREIGN PATENT DOCUMENTS

DE         43 06 119 A         9/1994

OTHER PUBLICATIONS

"Two Decades of Array Signal Processing Research—The Parametric Approach," H. Krim and M. Viberg, IEEE Signal Processing Magazine, Jul. 1996, pp. 67–94.

* cited by examiner

Primary Examiner—Bryan Bui
Assistant Examiner—Xiuqin Sun
(74) Attorney, Agent, or Firm—Ware, Fressola, Van Der Sluys & Adolphson LLP

(57) ABSTRACT

A method and corresponding system for measuring the speed of sound in a fluid contained within an elongated body, the sound transversing the elongated body substantially along a direction aligned with the longest axis of the elongated body, the method including the steps of: providing at predetermined locations an array of at least two sensors distributed along the elongated body, each sensor for discerning and signaling spatio-temporally sampled data including information indicating the pressure of the fluid at the position of the sensor; acquiring the spatio-temporally sampled data from each sensor at each of a number of instants of time; constructing a plot derivable from a plot, using a technique selected from the group consisting of spectral-based algorithms; identifying in the plot a spectral ridge, and determining the slope of the spectral ridge; and determining the speed of sound assuming a relation between the speed of sound and the slope of the spectral ridge.

4 Claims, 1 Drawing Sheet ns of US 6,587,798 B2

METHOD AND SYSTEM FOR DETERMINING THE SPEED OF SOUND IN A FLUID WITHIN A CONDUIT

CROSS REFERENCE TO RELATED APPLICATION

Reference is made to and priority claimed from U.S. provisional application Ser. No. 60/250,997, filed Dec. 4, 2000, entitled METHOD AND SYSTEM FOR DETERMINING THE SPEED OF SOUND IN A FLUID WITHIN A CONDUIT.

FIELD OF THE INVENTION

The present invention pertains to the field of processing acoustic signals, and more particularly to the field of measurements of the speed of sound in a medium of unknown constituents when the direction of propagation of the sound is known, such as when sound propagates in a fluid within a conduit.

BACKGROUND OF THE INVENTION

In extracting oil and gas from a formation, it is advantageous to monitor the flow rates of the different components of the production fluid, usually gas, oil and water. It has been established that measuring the sound speed of a mixture can be used to determine the volumetric phase fractions of the components since the speed of sound in a mixture can be directly related to the speed of sound in the components of the mixture.

Techniques for determining the speed at which a pressure disturbance travels along an array of sensors have been developed for use in many fields, such as the fields of sonar processing, radar, and seismic imaging. For example, in the field of underwater sonar signal processing, a technique called beam forming is used to determine the direction of approach (DOA) of an acoustic signal based on determining the speed at which the acoustic wave travels along the array. Knowing the speed of sound in the water and the speed at which the acoustic wave travels along the array enables the determination of the direction of approach of the acoustic signal. Many different processing techniques have been developed for use in such applications, techniques aimed at extracting from an array of sound detectors the speed at which a wave travels across an array of sensors. (See, e.g. "Two Decades of Array Signal Processing Research—the Parametric Approach," by H. Krim and M. Viberg, IEEE Signal Processing Magazine, pp. 67–94.)

In contrast to underwater sonar applications, in a production fluid flowing through a conduit, sound-producing disturbances occur continuously, as a natural consequence of the flow of the production fluid through the conduit, and their locations are not of interest. Therefore, in measuring the speed of sound in such a conduit in order for example to use the value of the speed of sound for some monitoring function, it is not necessary to provide a source of sound. Moreover, again in contrast to underwater sonar applications, the direction of travel of the essentially one-dimensional, planar sound waves within a conduit is known, i.e. the sound is either traveling upstream or downstream within a conduit. Thus, the problem of measuring the speed of sound in a fluid contained within a conduit has known values for a principal unknown of a sonar application, namely the direction of approach, but has as an unknown what is assumed in a sonar application, namely the speed of sound.

What is needed in many applications, including determining the speed of sound in a fluid within a conduit, is a way of adopting the methodologies of underwater sonar signal processing to what is essentially the inverse of the problem solved in that field, i.e. using information provided by an array of sound detectors to determine not the direction of approach to a sound source relative to the axis of the array in a 3-dimensional medium of known sound speed, but instead using the array of sensors to directly measure the speed of sound within a conduit in which the direction of approach is known to be aligned with an axis of the array.

SUMMARY OF THE INVENTION

Accordingly, the present invention provides a method and corresponding system for measuring the speed of sound in a fluid contained within an elongated body, the sound traversing the elongated body substantially along a direction aligned with the longest axis of the elongated body, the sound causing a momentary change in pressure in a portion of the fluid as the sound traverses the portion of the fluid, the method including the steps of: providing at predetermined locations an array of at least two sensors distributed along the elongated body, each sensor for discerning and signaling spatio-temporally sampled data including information indicating the pressure of the fluid at the position of the sensor; acquiring the spatio-temporally sampled data from each sensor at each of a number of instants of time; constructing a plot derivable from a plot, using a technique selected from the group consisting of spectral-based algorithms, such as the Capon method or the MUSIC method, in which a spectrum-like function of the speed of sound is formed, and parametric methods of solution, such as the deterministic maximum likelihood method; identifying in the plot a spectral ridge, and determining the slope of the spectral ridge; and determining the speed of sound assuming a relation between the speed of sound and the slope of the spectral ridge.

BRIEF DESCRIPTION OF THE DRAWINGS

The above and other objects, features and advantages of the invention will become apparent from a consideration of the subsequent detailed description presented in connection with accompanying drawings, in which.

BEST MODE FOR CARRYING OUT THE INVENTION

Figure 1:
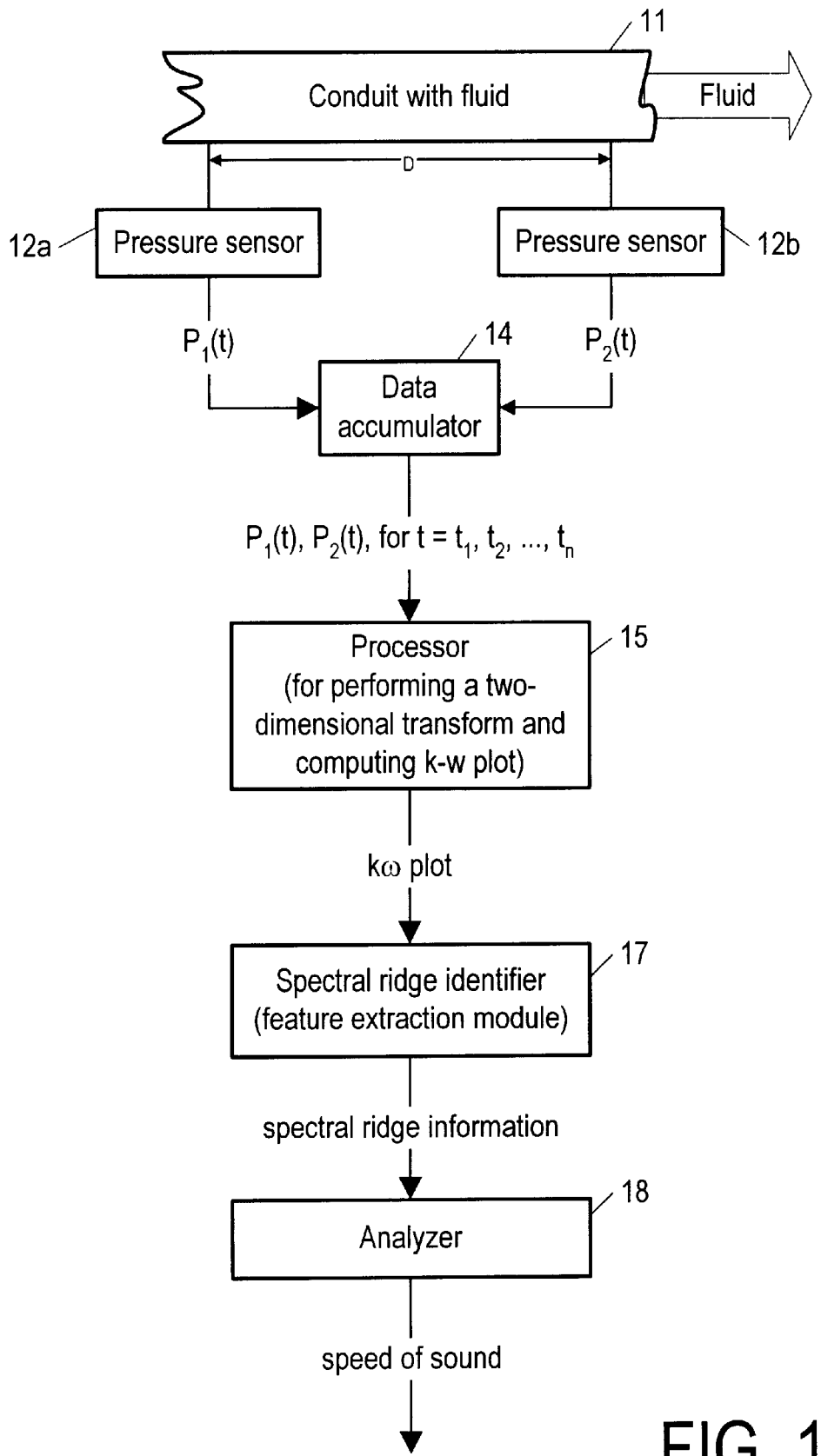
FIG. 1 is a schematic block diagram/flow diagram of a system according to the present invention for determining the speed of sound in a fluid within a conduit.

Referring now to FIG. 1, a system according to the invention for measuring the speed of sound in a fluid (liquid or gas or multiphase fluid) within a conduit 11 is shown as including at least two pressure sensors 12a 12b, constituting what is often called a phased array of sensors and providing signals indicating fluid pressure (or a phased array providing signals indicating any other parameter that can be correlated to acoustic disturbances, e.g. accelerometers or hotwires) at the location of the sensors at each of a number of successive instants of time. The outputs of each array in the array of sensors need to be recorded such that the time reference of each sensor is known relative to every other sensor. A data accumulator 14 receives the signals from the sensors 12a 12b over a period of time during which from each sensor some predetermined number n of signals $P_1(t_j), P_2(t_j)$ (for $j=1, \ldots, n$) are provided.

With the data so accumulated, in general, any one of the processing techniques used in beam-forming or other array processing applications that construct a two-dimensional temporal/spatial transform can then be used decompose the array of signals into its temporal and spatial bins, i.e. to provide what is called a kω plot. Such a plot is useful in visualizing a temporal/spatial decomposition.

Still referring to FIG. 1, in the preferred embodiment, the accumulated signals are then provided to a processor 15, which performs the spatial/temporal decomposition, and computes the kω plot, with k representing the wave number for a spectral component and ω representing the corresponding angular frequency. The propagating nature of the acoustic signals is such that all of the one-dimensional acoustic energy in the signal lies on a line in the kω plane. In a non-dispersive medium (i.e. non-dispersive for the spectral frequencies of interest so that all spectral components propagate at the same speed, the sought after speed of sound), the slope of this line is the speed of sound in the fluid, on account of the kinematic relationship ω=ck, where ω is the angular frequency of a spectral component of the acoustic disturbances, and k is the wavenumber, and c is the sought-after (unknown) speed of sound. To the extent that for high enough frequencies there is some dispersion, slight modifications to the spatial-temporal relation of acoustic wave can be included in the method according to the present invention to account for the dispersive effects, without fundamentally altering the concepts underlying the invention. Thus, the acoustic energy is distributed over a well-defined region (line) of the kω plane. If the acoustics are sufficiently energetic with respect to other disturbances, and the acoustics are significantly broad band, the acoustic signal will form a so called spectral ridge in a kω plot with the energy of each sector determining the height of the spectral ridge.

A kω plot therefore includes spectral ridges at a slope indicative of the speed of sound in the fluid. The slope of a ridge represents the speed of propagation of sound through the conduit containing the fluid. This sound speed is typically not the same as the sound speed of the same fluid in an infinite media; the compliance added by the conduit typically reduces the speed of sound. This effect can, however, be modeled, and through such modeling, the sound speed of the fluid in an infinite media can be inferred from the measurement of the sound speed of the fluid within the conduit. (See co-owned U.S. application having Ser. No. 09/344,094, filed Jun. 25, 1999, entitled "Fluid Parameter Measurement in Pipes Using Acoustic Pressures," for a more complete description of the effect of the conduit.)

In principle, depending on how far apart the sensors are positioned, a kω plot determined as above can also include spectral ridges indicative of the speed of sound through the conduit itself (i.e. the compression waves within the wall of a pipe, for example, as opposed to within the fluid in the conduit), a speed which is typically greater than the speed of sound in the fluid. However, it is possible to easily distinguish between the spectral ridge corresponding to the propagation of sound in the fluid compared to propagation through the conduit on the basis that the slopes of the corresponding spectral ridges are significantly different.

Once the kω plot is determined, a spectral ridge identifier 17 examines it to identify any spectral ridges it might reveal. Depending on the noise environment, spectral ridges may be discernible for sound propagating both upstream and downstream through the fluid in the conduit. Since as mentioned above, a kω plot includes measured data on time stationary sound (acoustic disturbances) and the spatial wavelength and the temporal frequency of a spectral component of the sound are related through the phase velocity c of the components according to $\lambda v = c$, the relation $\omega = ck$ follows by substituting $k = 2\pi/\lambda$, and $\omega = 2\pi v$ for $\lambda$ and $v$, respectively. Thus, a spectral ridge in a kω plot (i.e. a plot with k as the abscissa or x-coordinate and ω as the ordinate or y-coordinate) has a slope that is the average phase velocity of sound in the fluid. The spectral ridge identifier provides for each spectral ridge it identifies information sufficient to indicate a slope of the spectral ridge. An analyzer 18 uses the spectral ridge identifications to provide an overall assessment of the measured phase velocity in the fluid. In some situations, the sensors 12a 12b will sense a pure tone or set of pure tones and the corresponding k–ω plot will therefore not have a ridge, but instead only a portion of a ridge.

To the extent that the spectral ridge is straight, the phase velocity of sound is independent of frequency, i.e. there is no dispersion. Indeed, it is the case that there is little dispersion of sound in any fluid (gas or liquid) in an infinite medium over the frequency range typically employed in multiphase flow measurements (i.e. from approximately 10 Hz to approximately 2000 Hz). Thus, the average phase velocity as measured above, once corrected for the influence of the pipe, is an accurate estimate of the sound speed of the fluid.

It is helpful to consider the limited case in which the sound being sensed is a pure tone and is propagating in only one direction. In essence, in case of the passage of a single harmonic sound wave, a system according to the invention obtains information about the wavelength λ (or the wavenumber k) of the sound wave by sensing the phase of the sound wave at the two measurement points, a known distance separation D apart. Thus, the separation D can be determined to be a particular fraction of a wavelength of the sound.

The combination of the frequency information and the wavelength information yields the speed of sound. The information is only not ambiguous, however, if the sensors sample frequently enough (i.e. perform Nyquist sampling) to avoid temporal aliasing, and are close enough together to avoid spatial aliasing. For example, if the sensors are a distance D apart that is (undesirably) two wavelengths, the system would indicate a value for the wavelength that is twice the actual value.

Of course the sound picked up by the sensors 12a 12b is not harmonic; it is a superposition of many spectral components of one or more complex sound waves (one or more since more than one sound wave may reach the sensors at the same time), each complex sound wave including its own spectral components. The processor 15 performs a spectral analysis of the sound it detects so that what is plotted as a kω plot are the wavenumbers and angular frequencies for the different harmonic components of at least one complex sound wave.

The processor 15 accounts for the possibility of multiple complex signals contributing to the pressure signals provided by the sensors 12a 12b. The processor extracts from the sample points $P_1(t_j), P_2(t_j)$ provided by the data accumulator 14 information sufficient to determine the relationship, if any, between the sample points $P_1(t_j)$ provided by one sensor and the sample points $P_2(t_j)$ provided by the other sensors.

By way of illustration of one way of performing the two dimensional transform accomplished by the processor 15, a one-dimensional acoustic field including left-going and right-going (plane) waves is typically represented as, $$p(x, \omega) = A(\omega)e^{i\frac{\omega x}{c}} + B(\omega)e^{-i\frac{\omega x}{c}}, \qquad (1)$$

where x is the one-dimensional space variable, ω is temporal frequency, A and B give the frequency content of the right-going and left-going fields, i=√−1, and c is the speed of sound through the fluid. Equation (1) is valid for describing one dimensional acoustic disturbances in any region of a conduit (pipe) section in which acoustic energy is neither substantially created or destroyed (i.e. where it is reasonable to assume that there are no sound sources or sound absorbers).

Now in what is called the maximum likelihood method, the speed of sound is estimated according to a procedure that measures the degree to which a set of signals exhibits the spatial/temporal structure of equation (1), as follows. First, a data stream of pressure signals from spatially distributed sensors is taken. The excitation or noise sources that result in these signals is irrelevant, as long as acoustic pressure generation in the section of pipe where signals are measured is small compared to incoming noise, disturbances, or excitations. Next, the degree to which the data is consistent with the sound field properties represented in equation (1) is measured or estimated quantitatively, for various values of assumed sound speed c. This measure of consistency is here called the spatial/temporal consistency. Finally, the value of c which yields the highest spatial/temporal consistency is taken as the best estimate of the speed of sound based on the measurements.

The approach of the invention effectively isolates acoustic signals (via the spatial/temporal decomposition) from other signals that may exist in the fluid or be generated electrically by the measurement system. Even if such other signals are the result of traveling waves through other nearby media (such as the structure in which the pressure measurements are taken), the spatial/temporal structure of the acoustic signals is typically distinguishable for the different acoustic signals, and so can serve as a basis for providing a reliable estimate of the speed of sound in the fluid.

Although processing the data as described above can be performed in any spatio-temporal domain (such as the frequency/spatial ωx domain used in equation (1), the temporal/spatial tx domain, and the temporal/wavenumber tk domain), in the preferred embodiment, the frequency/wavenumber ωk domain is used. Equation (1) can be represented in the ωk domain by taking the spatial Fourier transform of equation (1), resulting in the following ωk representation:

$$p(k, \omega) = \qquad (2)$$
$$\frac{1}{2\pi}\int_{-\infty}^{\infty} p(x, \omega)e^{i\,kx}\,dx = A(\omega)\delta\!\left(k - \frac{\omega}{c}\right) + B(\omega)\delta\!\left(k - \frac{\omega}{c}\right)$$

where k is the wavenumber, and δ( . . . ) is the Dirac delta function.

Equation (2) shows the strong spatial/temporal structure of the acoustic field. In the kω plane, the function p(k,ω) consists of two ridges, one along the line k=ω/c and one along the line k=−ω/c. The present invention takes enough measurements to distinguish these ridges from other features of the measurement and so is able to deduce the value of the speed of sound c. The invention does so by performing a two dimensional transform of the sensor data, from the xt domain to the kω domain. The data is then analyzed, as explained above, to determine the speed of sound assuming that for each spectral component, k=ω/c. The invention comprehends any spectral or parametric method of performing the two-dimensional transform, including for example the CAPON method, the MUSIC method, and the deterministic maximum likelihood method. (See e.g. "Two Decades of Array Signal Processing Research—the Parametric Approach," by H. Krim and M. Viberg, mentioned above.) All such methods address handling the windowing (sampling) problem differently, and so some methods are better than others in particular situations.

The foregoing embodiments and illustrations having been described, it is to be understood that the above-described arrangements are only illustrative of the application of the principles of the present invention. Numerous other modifications and alternative arrangements may be devised by those skilled in the art without departing from the spirit and scope of the present invention, and the appended claims are intended to cover such modifications and arrangements.

What is claimed is:

1. A method for measuring the speed of sound c in a fluid contained within an elongated body, the sound traversing the elongated body substantially along a direction aligned with the longest axis of the elongated body, the sound causing a momentary change in pressure in a portion of the fluid as the sound traverses the portion of the fluid, the method comprising the steps of:

a) providing at predetermined locations an array of at least two sensors distributed along the elongated body, each sensor for discerning and signaling spatio-temporally sampled data including information indicating the pressure of the fluid at the position of the sensor;

b) acquiring the spatio-temporally sampled data from each sensor at each of a number of instants of time;

c) constructing a plot derivable from a kω plot, using a technique selected from the group consisting of spectral-based algorithms, such as the Capon method or the MUSIC method, in which a spectrum-like function of the speed of sound is formed, and parametric methods of solution, such as the deterministic maximum likelihood method;

d) identifying in the kω plot a spectral ridge, and determining the slope of the spectral ridge; and e) determining the speed of sound assuming a relation between the speed of sound and the slope of the spectral ridge.

2. A method as in claim 1, further comprising, before the step of constructing a plot derivable from a kω plot, the additional step of constructing for each sensor at least a portion of a time-dependent cross spectral density matrix, consisting of correlations of the spatio-temporally sampled data, at each of the number of instants of time, with the spatio-temporally sampled data of every sensor, in turn, including its own spatio-temporally sampled data.

3. A system for measuring the speed of sound c in a fluid contained within an elongated body, the sound traversing the elongated body substantially along a direction aligned with the longest axis of the elongated body, the sound causing a momentary change in pressure in a portion of the fluid as the sound traverses the portion of the fluid, the system comprising:

a) means for providing at predetermined locations an array of at least two sensors distributed along the elongated body, each sensor for discerning and signaling spatio-temporally sampled data including information indicating the pressure of the fluid at the position of the sensor;

b) means for acquiring the spatio-temporally sampled data from each sensor at each of a number of instants of time;
c) means for constructing a plot derivable from a kω plot, using a technique selected from the group consisting of spectral-based algorithms, such as the Capon method or the MUSIC method, in which a spectrum-like function of the speed of sound is formed, and parametric methods of solution, such as the deterministic maximum likelihood method;
d) means for identifying in the kω plot a spectral ridge, and determining the slope of the spectral ridge; and
e) means for determining the speed of sound assuming a relation between the speed of sound and the slope of the spectral ridge.

4. A system as in claim 3, further comprising means for constructing for each sensor at least a portion of a time-dependent cross spectral density matrix, consisting of correlations of the spatio-temporally sampled data, at each of the number of instants of time, with the spatio-temporally sampled data of every sensor, in turn, including its own spatio-temporally sampled data.

* * * * *

UNITED STATES PATENT AND TRADEMARK OFFICE
CERTIFICATE OF CORRECTION

PATENT NO. : 6,587,798 B2
DATED : July 1, 2003
INVENTOR(S) : Alan D. Kersey, Daniel L. Gysling and James D. Paduano It is certified that error appears in the above-identified patent and that said Letters Patent is hereby corrected as shown below:

Column 6,
Line 54, equation (2) "(k-w/c)" should read -- (k+ w/c) --.

Signed and Sealed this

Twenty-first Day of October, 2003

JAMES E. ROGAN
*Director of the United States Patent and Trademark Office*